United States Patent [19]
Winokur et al.

[11] Patent Number: 5,932,541
[45] Date of Patent: Aug. 3, 1999

[54] METHOD OF ADJUSTING THE CIRCADIAN RHYTHM OF A MAMMAL

[75] Inventors: Andrew Winokur, Merion, Pa.; Gary E. Pickard, Fort Collins, Colo.; Nedra A. Lexow, Philadelphia, Pa.; Keith A. Gary, Marlton, N.J.

[73] Assignee: Gruenenthal GmbH, Aachen, Germany

[21] Appl. No.: 09/051,860

[22] PCT Filed: Oct. 24, 1996

[86] PCT No.: PCT/US96/17183

§ 371 Date: Aug. 20, 1998

§ 102(e) Date: Aug. 20, 1998

[87] PCT Pub. No.: WO97/15301

PCT Pub. Date: May 1, 1997

Related U.S. Application Data

[60] Provisional application No. 60/006,047, Oct. 24, 1995.

[51] Int. Cl.$^6$ ..................................................... A61K 38/00
[52] U.S. Cl. ................................................................ 514/2
[58] Field of Search ................................... 514/2, 12, 416, 514/646

[56] References Cited

U.S. PATENT DOCUMENTS

| | | | |
|---|---|---|---|
| 4,045,556 | 8/1977 | Schwertner et al. | 424/177 |
| 4,600,723 | 7/1986 | Short et al. | 514/416 |
| 5,114,976 | 5/1992 | Norden | 514/646 |

*Primary Examiner*—Raymond Henley, III
*Attorney, Agent, or Firm*—Everson, McKeown, Edwards & Lenahan, P.L.L.C.

[57] ABSTRACT

A method of adjusting the circadian rhythm of a mammal comprising administering to said an effective circadian rhythm adjusting amount of 6-methyl-5-oxo-3-thiomorpholinylcarbonyl-L-histidyl-L-prolinamide or a pharmaceutically acceptable salt thereof is disclosed. The method of the invention may be useful to assist shift workers adjust to rotating work schedules, to alleviate the effects of jet-lag on travelers to remote time zones and/or to treat sufferers of delayed sleep phase syndrome.

19 Claims, No Drawings

5,932,541

METHOD OF ADJUSTING THE CIRCADIAN RHYTHM OF A MAMMAL

This application claims benefits under 35 USC 119(e) over U.S. Provisional Application 60/006,047 filed Oct. 24, 1995.

BACKGROUND OF THE INVENTION

It is well established that living organisms have internal biological clocks which regulate activities such as their sleep/wake cycles. These biological clocks are expressions of the effects of one or more endogenous pacemakers thought to be located in the suprachiasmatic nuclei (SCN) of the hypothalamus. The activity sequences defined by these internal biological clocks are referred to as circadian rhythms. Different organisms have different circadian cycles. Creatures which tend to be active during periods of daylight and inactive at night are termed diurnal. Creatures which are active at night and sleep during the day are referred to as nocturnal. In general, natural circadian rhythms are entrained by and tend to follow the natural sequence of daytime light and nighttime darkness which occurs as the earth rotates. For further information see Moore, R. Y., in *Sleep and Biological Rhythms*, (Montplasir, J. & Godbout, R., eds.), pages 3–10, Oxford Univ. Press (1990).

Under normal circumstances, the circadian rhythm of humans serves as a useful time regulator of various activities. In some instances, however, the internal circadian clock interferes with desired adaptations to differing time schedules. For example, air travelers who rapidly cross two or more time zones may find their internal circadian clocks out of phase with the day/night cycle at their destination, giving rise to the so-called "jet-lag" syndrome in which they suffer disruptions of their sleep patterns and diminished attention span and alertness until their inner biological clocks gradually adjust to local time. Shift workers, whose work schedules rotate among day shift, night shift and the so-called "graveyard" shift, may experience transient internal temporal dissociation or a lack of synchronization among various bodily rhythms, and consequent difficulty in adjusting to shift changes. This can not only adversely affect worker productivity, but in some instances may raise safety concerns. In addition, some persons suffer from circadian irregularities such as insomnia or advanced or delayed sleep phase syndrome which interfere with maintenance of normal activity pattern.

Various approaches have been attempted to adjust circadian rhythms. For example, it has been discovered that exposure to sufficiently bright light at appropriate times in the circadian cycle can advance or delay the circadian rhythm. In addition, attempts have been made to use chemical agents, such as melatonin, to advance or delay the circadian rhythm of an organism, see Lewy et al., *Chronobiology International*, Vol. 9, No. 5, pp 380–392 (1992). Despite much effort in the prior art, however, there has remained a substantial need for methods to adjust the circadian rhythm of a mammal.

SUMMARY OF THE INVENTION

Accordingly, it is the object of the present invention to provide a new method for adjusting the circadian clock of a mammal.

A further object of the invention is to provide an effective pharmacotherapeutical method for adjusting the circadian rhythm of a mammal.

Another object of the invention is to provide a method for adjusting the circadian clock of a mammal which can be used to enable shift workers to adjust to work schedule changes or to treat conditions such as jet-lag or circadian irregularities such as displaced sleep phase syndrome.

These and other objects of the invention are achieved in accordance with the present invention by providing a method of adjusting the circadian rhythm of a mammal comprising administering to said mammal an effective circadian clock adjusting amount of 6-methyl-5-oxo-3-thiomorpholinylcarbonyl-L-histidyl-L-prolinamide.

In accordance with a further aspect of the invention, the objects are achieved by providing a method of adjusting the circadian clock of a mammal to a waking/sleeping cycle out of phase with normal light/dark exposure of day and night comprising administering an effective circadian rhythm advancing amount of 6-methyl-5-oxo-3-thiomorpholinylcarbonyl-L-histidyl-L-prolinamide to the mammal from 0 to 12 hours, preferably from 0 to 8 hours, (e.g. from 1 to 4 hours), prior to onset of a desired waking period.

In another aspect of the invention, the objects are achieved by providing a method of adjusting the circadian clock of a mammal traveling to a remote time zone to a cycle of wakefulness and sleep corresponding respectively to day and night of said remote time zone comprising administering to the mammal an effective circadian rhythm advancing amount of 6-methyl-5-oxo-3-thiomorpholinylcarbonyl-L-histidyl-L-prolinamide from 0 to 12 hours, preferably from 0 to 8 hours, (e.g. from 1 to 4 hours), prior to onset of daylight in the remote time zone.

And in accordance with yet another aspect of the invention, the objects are achieved by providing a method of treating a mammal having a circadian rhythm out of phase with cycles of daylight and night prevailing where the mammal is located comprising administering to the mammal an effective circadian rhythm advancing amount of 6-methyl-5-oxo-3-thiomorpholinylcarbonyl-L-histidyl-L-prolinamide from 0 to 12 hours, preferably from 0 to 8 hours, (e.g. from 1 to 4 hours), prior to onset of daylight.

DETAILED DESCRIPTION OF PREFERRED EMBODIMENTS

The preferred active form of 6-methyl-5-oxo-3-thiomorpholinylcarbonyl-L-histidyl-L-prolinamide is (3R,6R)-N-[(6-methyl-5-oxo-3-thiomorpholinyl)carbonyl]-L-histidyl-L-prolinamide tetrahydrate. For convenience, 6-methyl-5-oxo-3-thiomorpholinylcarbonyl-L-histidyl-L-prolinamide -L-histidyl-L-prolinamide will be referred to hereinafter by its international, non-proprietary name, Montirelin.

Montirelin is a known compound which exhibits central nervous system stimulating effects. It has been suggested for possible use as an anti-depressant or in the treatment of loss of consciousness caused by head concussion. The preparation of this compound is described e.g. in Schwertner et al., U.S. Pat. No. 4,045,556, the disclosure of which is incorporated herein by reference.

Montirelin may be administered in various ways. For reasons of patient convenience, orally or nasally administrable forms are desirable. It may also be successfully administered by intramuscular, intraperitoneal or intravenous injection of sterile solutions. Preferred dosages may range from about 0.05 mg/kg/day to about 50 mg/kg/day, e.g. 10 mg/kg/day to 20 mg/kg/day. Dosages in the range from about 200 µg/kg/day to about 400 µg/kg/day are particularly preferred. It is understood that the optimum dosage may vary depending on the patient and the severity of the condition being treated, and it is considered within the skill of the art to optimize the dosage within the indicated range.

The active substance may be administered as such as a free base or in the form of a salt with a pharmaceutically acceptable inorganic acid, such as hydrochloric acid, sulfuric acid or phosphoric acid, or organic acid such as acetic acid, benzoic acid, maleic acid, fumaric acid, tartaric acid, benzene sulfonic acid, etc.

The active substance may be formulated in the form of sterile solutions or in tablets, capsules, dragees, syrups, granules, suppositories, sprays, etc. with various known pharmaceutical carriers or diluents such as water, mineral oil, syrups, polyethylene glycol, lactose, corn starch, paraffin and the like, and may be mixed with known adjuvants such as stabilizers, suspending agents, binders, viscosity improvers, flavors, coloring agents, preservatives, etc.

For purposes of illustration, useful dosage forms may be prepared as follows:

Example Oral Tablet Formulation

Tablets may be prepared comprosing the following ingredients in parts by weight:

| Montirelin | 10 parts |
|---|---|
| lactose monohydrate | 64 parts |
| corn starch | 20 parts |
| polyvinylpyrrolidone (Polyvidone K 30) | 5 parts |
| magnesium stearate | 1 part |

The active compound, lactose monohydrate and corn starch are sieved through a 0.63 mm sieve, mixed in a cube blender for 10 minutes, granulated with an aqueous solution of polyvinylpyrrolidone in water (50 g in 200 ml of water), dried, sized through an 0.8 mm sieve together with the magnesium stearate, mixed and pressed into tablets having a diameter of 6 mm and an average weight of 100 mg using a conventional tablet press such as a Korsch EK 0 eccentric press.

Example Oral Liquid Formulation

An orally administrable liquid formulation may be prepared comprising the following ingredients in parts by weight:

| Montirelin | 10 parts |
|---|---|
| potassium sorbate | 10 parts |
| sodium citrate | 6 parts |
| citric acid | 2 parts |
| sodium chloride | 2 parts |
| sucrose | 200 parts | sufficient water to make desired solution volume containing 10 g Montirelin per liter of solution.

The solid ingredients were all dissolved in water, filtered through a 0.23 μm membrane and filled into bottles. 1 ml of the resulting solution contained 10 mg of Montirelin. Individual dosing can be achieved by administering individual volumes of the solution to the patient.

Example Nasal Spray Formulation

A nasal spray formulation may be prepared comprising the following ingredients in parts by weight:

| Montirelin | 80 parts |
|---|---|
| benzalkonium chloride | 1 part |
| polyoxyethylene (20) sorbitan monooleate (polysorbate 80) | 80 parts |
| sodium carboxymethylcellulose (Tylose ™ C 30) | 80 parts |
| disodium hydrogen phosphate | 72 parts |
| sodium dihydrogen phosphate | 32 parts |
| dextrose | 240 parts | purified water to make desired solution volume containing 10 g Montirelin per liter of solution.

The solid ingredients were all dissolved in the water, filtered through a 0.5 μm membrane and, filled into bottles topped by a spray pump with a volumetric dispensing chamber of 100 μl for nasal administration.

Toxicity

The subacute repeated-dose intravenous toxicity of Montirelin was investigated in Sprague-Dawley rats treated repeatedly at 0.05, 0.5,5 and 50 mg/kg/day for five weeks, and the reversibility of its toxic effects was also investigated by a four-week recovery study.

Eight nine SPF Slc:SD rats of both sexes (age: four weeks, body weight: 70.0–81.6 g) were purchased from Shizuoka Agriculture Cooperative Association for Laboratory Animals. During a one-week quarantine/acclimation period, the animals were measured for body weight and observed for any general symptoms, and healthy animals showing normal growth were selected and used in the experiment at the age of five weeks.

Males and females were used in five groups (including the control group) of 10 animals/sex, and additional 10 animals/sex ere added to the control, 0.5 mg/kg and 50 mg/kg groups to investigate the reversibility of the toxic effect of the test substance. All these animals were randomized to each group by weight stratification so that the differences in initial mean body weight were within 2% between groups. At the start of the treatment, the body weight was 116.5–132.9 g for males and 107.0–123.4 g for females.

The maximal dose was set at 50 mg.kg which is three lower doses were set at 5, 0.5 and 0.05 mg/kg using a common ratio of 1/10. This study also included the vehicle control group.

The experimental design (doses, number of animals/group and concentrations of the dosing solution) is presented in Table I.

TABLE I

Subacute toxicity study of Montirelin in rats

| | | | | Volume of Test Substance | |
|---|---|---|---|---|---|
| Sex | Group | Number of animals | | (ml/Kg) | (W/V%) |
| | Administration period (5 weeks) Recovery period (4 weeks) | | | | |
| Male | Control* | 20 | 10 | 5 | 0 |
| | 0.0 mg/kg | 10 | — | 5 | 0.001 |
| | 0.5 mg/kg | 20 | 10 | 5 | 0.01 |
| | 5 mg/kg | 10 | — | 5 | 0.1 |
| | 50 mg/kg | 20 | 10 | 5 | 1 |
| Female | Control* | 20 | 10 | 5 | 0 |
| | 0.0 mg/kg | 10 | — | 5 | 0.001 |

TABLE I-continued

Subacute toxicity study of Montirelin in rats

| Sex | Group | Number of animals | Volume of Test Substance | |
|---|---|---|---|---|
| | | | (ml/Kg) | (W/V%) |
| | 0.5 mg/kg | 20 | 10 | 5 | 0.01 |
| | 5 mg/kg | 10 | — | 5 | 0.1 |
| | 50 mg/kg | 20 | 10 | 5 | 1 |

*physiological saline

Dosing solutions were prepared by dissolving a weighed amount of the test substance in physiological saline at a concentration of 1 W/V % using a volumetric flask. Lower dosing solutions were obtained by successive 10-fold dilution of the initial solution. The respective dosing solution was repeatedly administered intravenously once daily for 35 days into the tail vein at a rate of 0.2 ml/10 sec. using a ¼ syringe for injection. The treatment was given at a constant volume of 0.5 ml/100 g body weight in all dose groups, and the control group was treated with physiological saline at the same volume in the same manner.

Clinical signs in all animals were observed daily between two and four hours after dosing according to Irwin's method of comprehensive observational assessment, and the type, severity, onset time and disappearance time of toxic symptoms were recorded. During the recovery period, the clinical observation was performed once daily in the morning in the same manner. The body weight, food consumption and water consumption were measured in all animals three times weekly in the morning throughout the treatment and recovery periods and recorded.

Throughout the administration and recovery periods, no death occurred in any treatment or control groups.

1. In the 50 mg/kg group, systemic tremor was observed transiently during the injection in both sexes form day 0 (the initial dosing day), but this symptom gradually regressed from day 1 with increasing day of treatment, disappearing by day 6 in males and by day 4 in females. In the 5 mg/kg or higher groups, almost all males and females showed transient polyuria, and this effect peaked at about one hour after dosing from day 0–3. However, this symptom also regressed as the treatment day increased, disappearing by day 4–28. There were no other remarkable clinical signs throughout the administration and recovery periods.

2. The water consumption increased in both sexes receiving 5 mg/kg or above from day 2–3 until about week 4. Treated males tended to decrease food consumption as compared with the control males, and, reflecting this effect, the body weight gain was suppressed in males, particularly those receiving 0.5, 5 and 50 mg/kg. In females, changes in food consumption and body weight were unremarkable.

3. The urinary findings were unremarkable except for an increase in urine volume in males receiving 5 mg/kg or above and females receiving 5 mg/kg or above at week 2 and 5 of treatment.

4. Hematologically, both sexes receiving 50 mg/kg showed increasing tendency in red blood cell count, hemoglobin and hematocrit to increase and decreasing tendency in total white blood cell count. However, all these changes were within the range of normal physiological variations. Changes in other hematological parameters were not related to the dose.

5. No treatment-related abnormalities were observed in the blood biochemical parameters.

6. At autopsy, no treatment-related grossly abnormal changes ere observed. Histopathologically, the incidence of hypertrophy of serous cells in the submaxillary gland showed dose-dependency in both sexes of all treatment groups. In other organs, no remarkable changes were shown at the light microscopic level, nor were there any abnormal changes in the liver or kidney at the electron microscopical examination.

All observed changes were reversed by discontinuing administration of the active compound.

EXAMPLE

Effects of Peripheral Montirelin Administration on Circadian Phase of Hamster Wheel Running Activity A preliminary study was conducted to determine whether peripherally administered 6-methyl-5-oxo-3-thiomorpholinyl-carbonyl-L-histidyl-L-prolinamide (Montirelin) is capable of phase shifting the circadian rhythm of hamster wheel running activity. Twenty-four male hamsters [Mesocricetus auratus; 8–12 weeks of age; Charles River LAK:LVG(SYR)] were housed individually in cages equipped with running wheels, and food and water freely available. Animals were maintained in light-tight, ventilated cabinets (six cages per cabinet) in which the lighting schedule could be controlled. Each animal's wheel running activity was monitored continuously throughout each experiment using a data acquisition software kit (Chronobiology, Stanford, Calif.).

Animals were maintained initially in a 14:10 hour light-:dark cycle for 7–10 days, then transferred to constant dim red lighting (RR) conditions for the remainder of the experiment (40–60 days). After free-running for 7 days in dim red lighting, animals either received Montirelin or vehicle intraperitoneally. The daily onset of wheel-running activity was defined as circadian time 12 (CT 12), and this time was used as a reference point in determining appropriate circadian injection times. The test animals were divided into eight groups of three animals each, and intraperitoneal injections of the active compound at dosage levels of 10 or 20 mg/kg or of the vehicle alone were administered to respective test groups at circadian time 3 (CT 3) or circadian time 16 (CT 16). The order of injections and time points was randomized. An additional 4 animals maintained in similar lighting conditions were visually observed for two hours post-injection of Montirelin (10 or 20 mg/kg) to determine any overt behavioral effects exerted by this compound. A total of 9 injections were made for each of the eight treatment groups.

Phase shifts in the circadian activity rhythm were determined by measuring the phase difference between eye-fitted lines connecting the onset of activity for a period of ten days before and ten days after an experimental manipulation. Beginning on the fifth day after treatments that caused phase advances and the second day after treatment that resulted in phase delays, an individual blinded to injection status evaluated the activity records.

Hamsters receiving 10 mg/kg Montirelin at CTs 3 and 16 showed no differences in overt behavior from animals receiving only vehicle at the same time points. Animals at CT 3 initially exhibited nesting behavior following injection and subsequently appeared to sleep through 90% of the observation period. Animals receiving drug or vehicle at CT 16 were more active in exploratory activities and wheel running activity, although no obvious differences were noted between drug and vehicle treatment groups. Wheel running activity accounted for approximately 55% of the study period in both drug and vehicle treatment groups.

In contrast, hamsters receiving 20 mg/kg Montirelin at both CT 3 and CT 16 demonstrated clear differences in overt behaviors from those observed in vehicle treated hamsters. Drug-treated animals exhibited frequent "wet dog" shakes, hypersalivation, rearing, tremor of the rear limbs, and were hyperactive in engaging in exploratory activity. While clearly in a state of heightened activity, drug-treated hamsters rarely mounted the running wheel at either circadian time (approx. 5% of observation period versus 0% and 52% in vehicle treated animals at CT 3 and 16, respectively). The effects of 20 mg/kg Montirelin were first noted at 25 minutes post-injection, and appeared maximal at 80 minutes after drug administration. Animals continued to show Montirelin-induced behaviors at the end of the two hour observation period, although their intensities were diminished.

The observed effects on the phase of wheel running activity as a average for each test group is shown in the following table:

| Effects on the Phase of Wheel Running Activity Group Averages (minutes) | | |
|---|---|---|
| Circadian Time | CT 3 | CT 16 |
| 10 mg/kg Montirelin | 4.3 ± 2.2 | 3.5 ± 2.3 |
| Vehicle only | 2.3 ± 1.6 | 3.4 ± 1.2 |
| 20 mg/kg Montirelin | 5.5 ± 2.4 | 3.1 ± 2.0 |
| Vehicle only | 4.2 ± 2.3 | 3.0 ± 1.7 |

Despite the small number of test animals and lack of rigorous statistical significance between the averages of specific treatment groups, promising phase delays (≈10 min.) and advances (≈16 min.) were observed in individual hamsters treated with Montirelin (20 mg/kg) at both CT 3 and CT 16, while no such phase shafts were observed in vehicle-treated controls.

The effect of Montirelin administration on the circadian rhythm necessarily will vary depending on the nature of the mammal and the identity of the condition treated. The effect also may vary depending on the time of administration. Administration from 0 to 12 hours, preferably from 0 to 8 hours, (e.g. from 1 to 4 hours), prior to onset of a normal activity period may advance the circadian clock of the patient. On the other hand, administration from 0 to 12 hours, preferably from 0 to 8 hours, (e.g. from 1 to 4 hours), prior to the end of a normal activity period may prolong the activity period and retard the circadian clock of the patient. Appropriate administration times for a given type of patient and condition to be treated may be determined in any given case by routine experimentation.

In practice, Montirelin may be administered in a single daily dose of from 0.1 to 50 μg, preferably from 1 to 5 μg, per kilogram of mammal body weight.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of adjusting the circadian rhythm of a mammal comprising administering to said mammal an effective circadian clock adjusting amount of 6-methyl-5-oxo-3-thiomorpholinylcarbonyl-L-histidyl-L-prolinamide or a pharmaceutically acceptable salt thereof.

2. A method according to claim 1, wherein 6-methyl-5-oxo-3-thiomorpholinylcarbonyl-L-histidyl-L-prolinamide or a pharmaceutically acceptable salt thereof is administered in a single daily dose from 0 to 12 hours prior to onset of normal light exposure of said mammal.

3. A method according to claim 1, wherein 6-methyl-5-oxo-3-thiomorpholinylcarbonyl-L-histidyl-L-prolinamide or a pharmaceutically acceptable salt thereof is administered in a single daily dose from 0 to 12 hours prior to onset of normal waking activity of said mammal.

4. A method according to claim 1, wherein said mammal is a nocturnal mammal.

5. A method according to claim 1, wherein said mammal is a diurnal mammal.

6. A method according to claim 1, wherein 6-methyl-5-oxo-3-thiomorpholinylcarbonyl-L-histidyl-L-prolinamide or a pharmaceutically acceptable salt thereof is administered in a single daily dose timed to advance the circadian clock of the mammal.

7. A method according to claim 1, wherein 6-methyl-5-oxo-3-thiomorpholinylcarbonyl-L-histidyl-L-prolinamide or a pharmaceutically acceptable salt thereof is administered in a single daily dose timed to delay the circadian clock of said mammal.

8. A method according to claim 1, wherein 6-methyl-5-oxo-3-thiomorpholinylcarbonyl-L-histidyl-L-prolinamide or a pharmaceutically acceptable salt thereof is administered in a single daily dose of from 0.1 to 50 μg per kg of mammal body weight.

9. A method according to claim 8, wherein 6-methyl-5-oxo-3-thiomorpholinylcarbonyl-L-histidyl-L-prolinamide or a pharmaceutically acceptable salt thereof is administered in a single daily dose of from 1 to 5 μg per kg of mammal body weight.

10. A method according to claim 1, wherein 6-methyl-5-oxo-3-thiomorpholinylcarbonyl-L-histidyl-L-prolinamide or a pharmaceutically acceptable salt thereof is administered orally.

11. A method according to claim 1, wherein 6-methyl-5-oxo-3-thiomorpholinylcarbonyl-L-histidyl-L-prolinamide or a pharmaceutically acceptable salt thereof is administered intraperitoneally.

12. A method according to claim 11, wherein 6-methyl-5-oxo-3-thiomorpholinylcarbonyl-L-histidyl-L-prolinamide or a pharmaceutically acceptable salt thereof is administered by intramuscular injection.

13. A method according to claim 11, wherein 6-methyl-5-oxo-3-thiomorpholinylcarbonyl-L-histidyl-L-prolinamide or a pharmaceutically acceptable salt thereof is administered by intranasal inhalation.

14. A method according to claim 11, wherein 6-methyl-5-oxo-3-thiomorpholinylcarbonyl-L-histidyl-L-prolinamide or a pharmaceutically acceptable salt thereof is administered intravenously.

15. A method of adjusting the circadian clock of a mammal to a waking/sleeping cycle out of phase with normal light/dark exposure of day and night, said method comprising administering an effective circadian rhythm advancing amount of 6-methyl-5-oxo-3-thiomorpholinylcarbonyl-L-histidyl-L-prolinamide or a pharmaceutically acceptable salt thereof to said mammal from 0 to 12 hours prior to onset of a desired waking period.

16. A method of adjusting the circadian clock of a mammal traveling to a remote time zone to a cycle of wakefulness and sleep corresponding respectively to day and night of said remote time zone, said method comprising administering to said mammal an effective circadian rhythm advancing amount of 6-methyl-5-oxo-3-thiomorpholinylcarbonyl-L-histidyl-L-prolinamide or a pharmaceutically acceptable salt thereof from 0 to 12 hours prior to onset of daylight in said remote time zone.

17. A method of treating a mammal having a circadian rhythm out of phase with cycles of daylight and night prevailing where said mammal is located, said method comprising administering to said mammal an effective circadian rhythm advancing amount of 6-methyl-5-oxo-3-thiomorpholinylcarbonyl-L-histidyl-L-prolinamide or a pharmaceutically acceptable salt thereof from 0 to 12 hours prior to onset of daylight.

18. A method according to claim 17, wherein said mammal is suffering from jet-lag.

19. A method according to claim 17, wherein said mammal is suffering from delayed sleep phase syndrome.

* * * * *